US011819367B2

(12) United States Patent
Jeong

(10) Patent No.: US 11,819,367 B2
(45) Date of Patent: Nov. 21, 2023

(54) NECKBAND TYPE MEDICAL HEADLIGHT SYSTEM

(71) Applicant: Jai Joon Jeong, Seoul (KR)

(72) Inventor: Jai Joon Jeong, Seoul (KR)

(73) Assignee: Jai Joon Jeong, Seoul (KR)

( * ) Notice: Subject to any disclaimer, the term of this patent is extended or adjusted under 35 U.S.C. 154(b) by 0 days.

(21) Appl. No.: 17/520,298

(22) Filed: Nov. 5, 2021

(65) Prior Publication Data

US 2022/0241046 A1 Aug. 4, 2022

(30) Foreign Application Priority Data

Jan. 29, 2021 (KR) ........................ 10-2021-0013144

(51) Int. Cl.
*A61B 90/30* (2016.01)
*A61B 90/35* (2016.01)
*H05B 47/105* (2020.01)
*H05B 47/175* (2020.01)
*A61B 90/50* (2016.01)
*A61B 90/00* (2016.01)
*A61B 17/00* (2006.01)
(Continued)

(52) U.S. Cl.
CPC .............. *A61B 90/30* (2016.02); *A61B 90/35* (2016.02); *H05B 47/105* (2020.01); *H05B 47/175* (2020.01); *A61B 5/1114* (2013.01); *A61B 2017/00119* (2013.01); *A61B 2017/00207* (2013.01); *A61B 2017/00734* (2013.01); *A61B 2017/00973* (2013.01); *A61B 2034/2048* (2016.02); *A61B 2090/3616* (2016.02); *A61B 2090/502* (2016.02); *A61B 2560/0214* (2013.01); *A61B 2560/0487* (2013.01); *A61B 2562/0219* (2013.01)

(58) Field of Classification Search
CPC .................. A61B 90/30; A61B 5/1114; A61B 2017/0027; A61B 2017/00734; A61B 2017/00973
See application file for complete search history.

(56) References Cited

U.S. PATENT DOCUMENTS

| 10,061,352 B1 * | 8/2018 | Trail ................... G02B 27/0172 |
| 2016/0070110 A1 * | 3/2016 | Ushakov .............. H04N 5/2251 |
| | | 348/373 |
| 2018/0228403 A1 * | 8/2018 | Li ........................ A61B 5/7405 |

(Continued)

FOREIGN PATENT DOCUMENTS

| CN | 208621835 U | * | 3/2019 |
| KR | 10-2015-0111198 A | | 10/2015 |

(Continued)

OTHER PUBLICATIONS

Machine Translation of Li (CN208621835) (Year: 2019).*

*Primary Examiner* — Leah Simone Macchiarolo
(74) *Attorney, Agent, or Firm* — IP & T GROUP LLP

(57) ABSTRACT

A neckband-type medical headlight system includes a lighting unit and a magnifying glass provided in glasses or a headset, a control unit configured to control the lighting unit, and a battery and a power cable configured to supply electric power to the lighting unit. The control unit for controlling the lighting unit is composed of a neckband type to be seated around a user's neck. A pedal-type wireless control unit is further provided to enable a user to turn on and off the lighting unit using a foot.

6 Claims, 13 Drawing Sheets

(51) Int. Cl.
  *A61B 34/20* (2016.01)
  *A61B 5/11* (2006.01)

(56) References Cited

U.S. PATENT DOCUMENTS

2019/0105784 A1* 4/2019 Hodges .................. G06F 1/163
2021/0140593 A1* 5/2021 Nguyen ................ F21V 23/001

FOREIGN PATENT DOCUMENTS

KR    10-2019-0096929 A    8/2019
KR        10-2438151 B1    8/2022

* cited by examiner

[FIG. 1] Prior Art
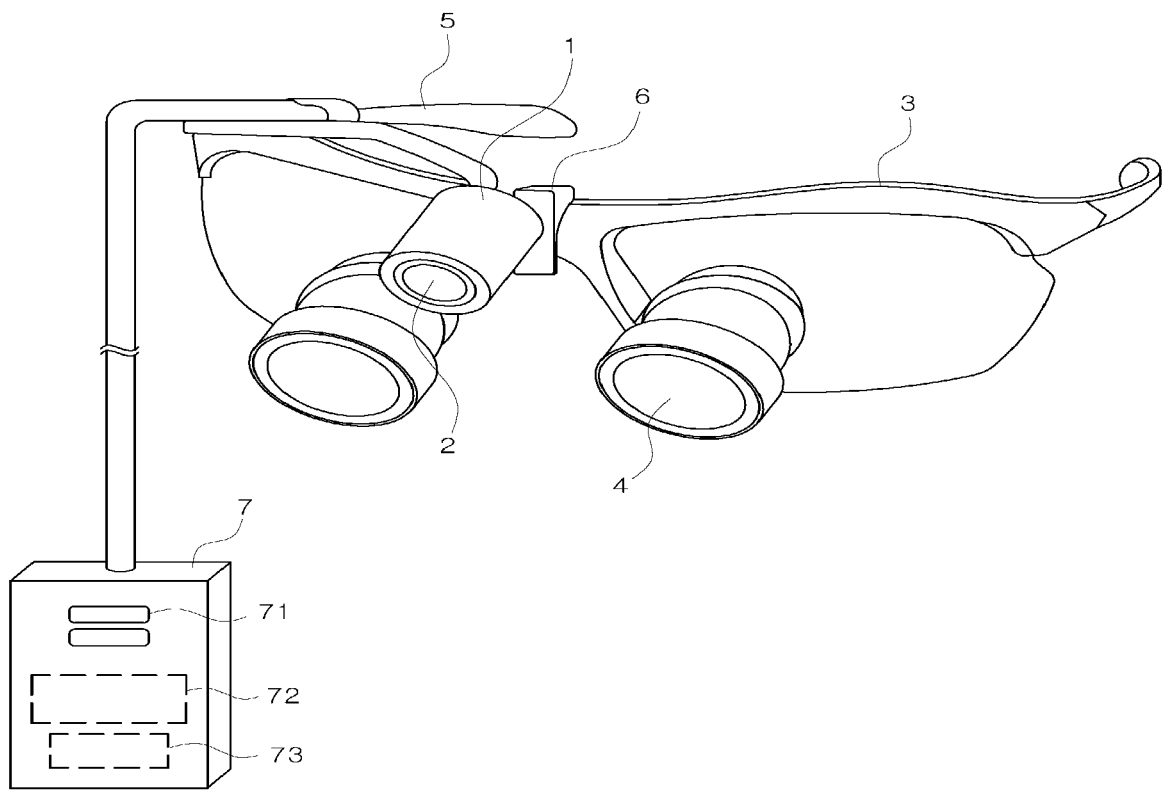

[FIG. 2] Prior Art
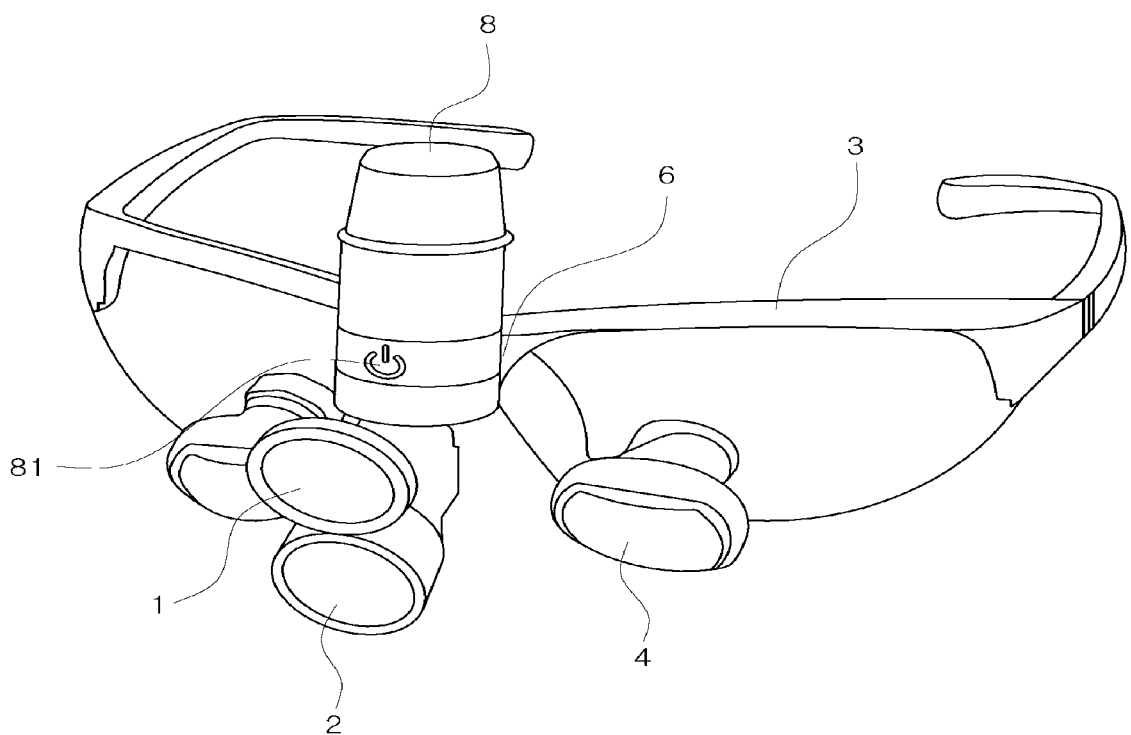

[FIG. 3]
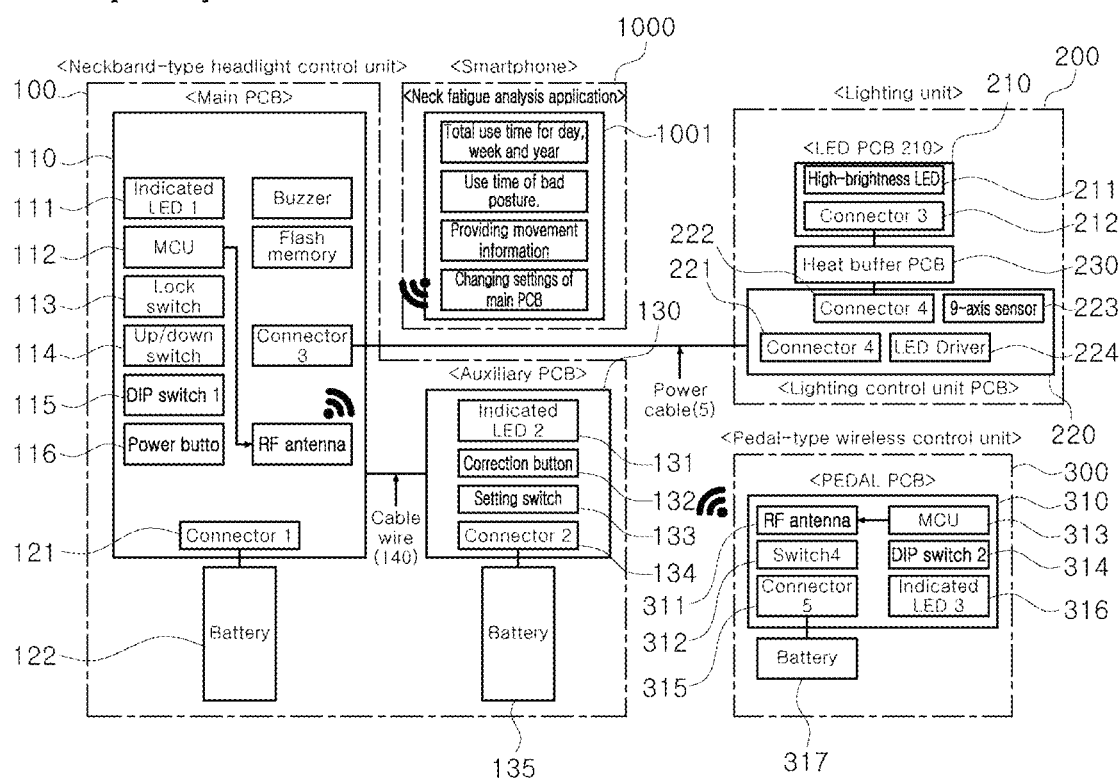

[FIG. 4]
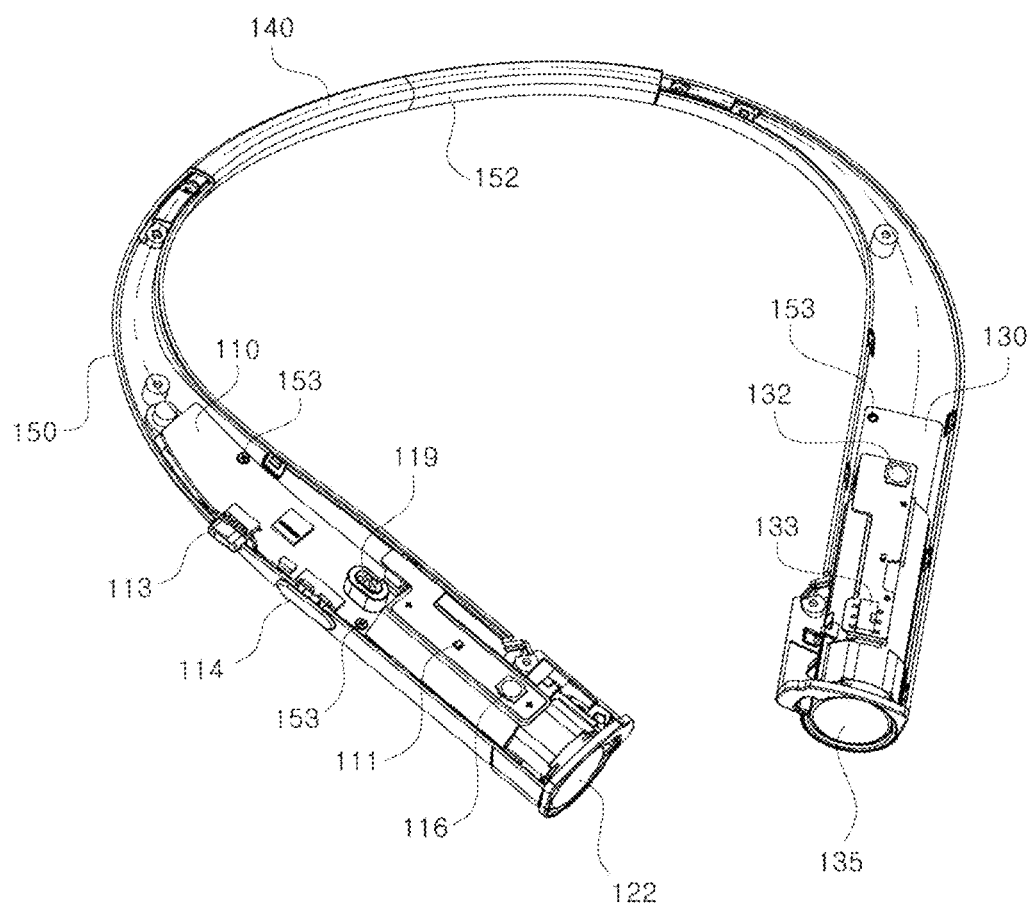

[FIG. 5]
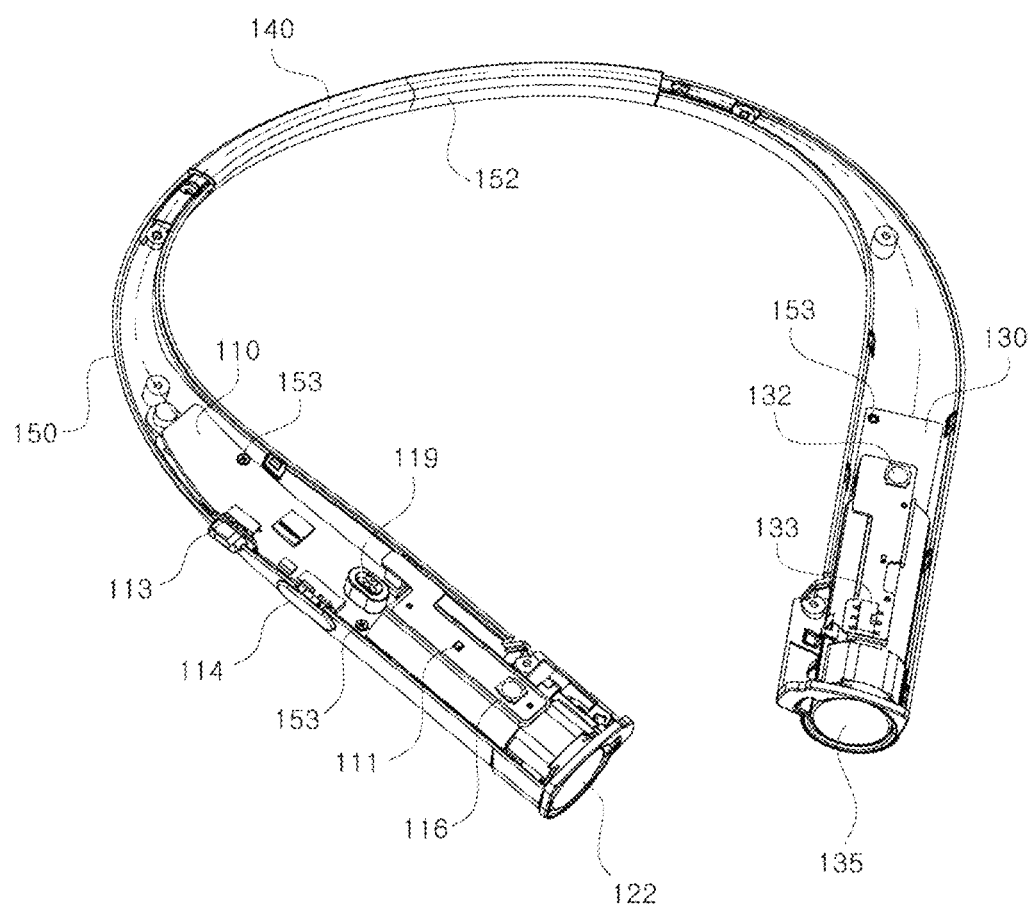

[FIG. 6]
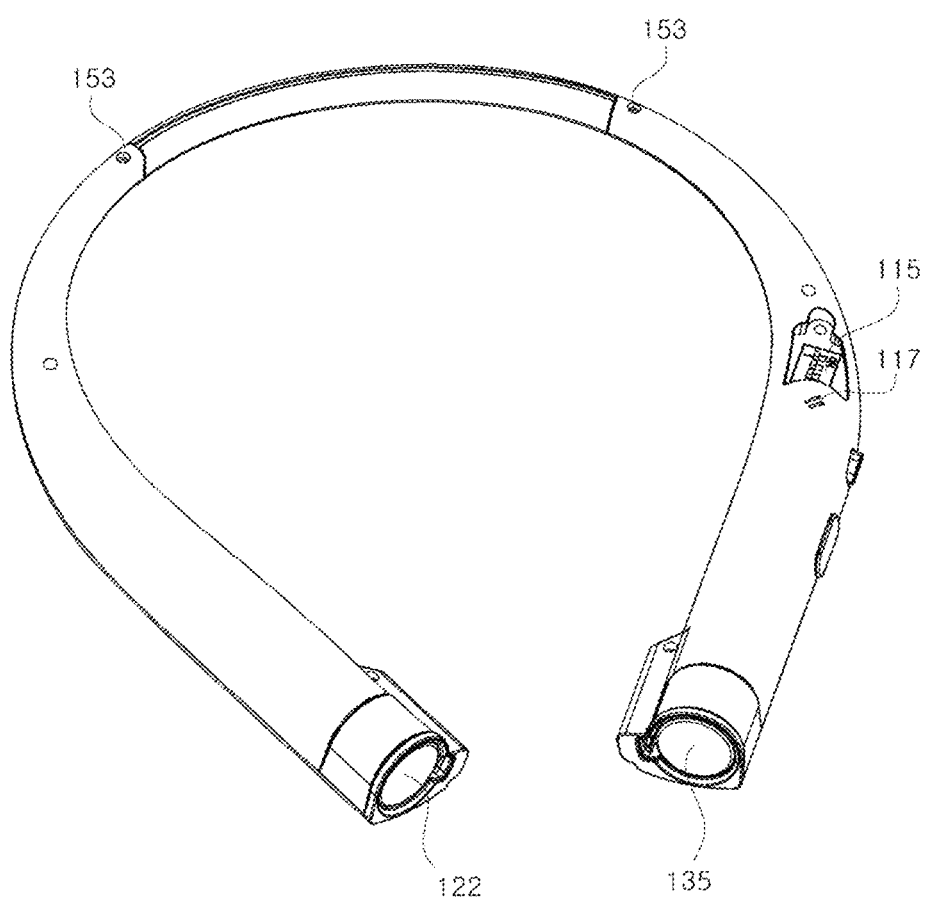

[FIG. 7]
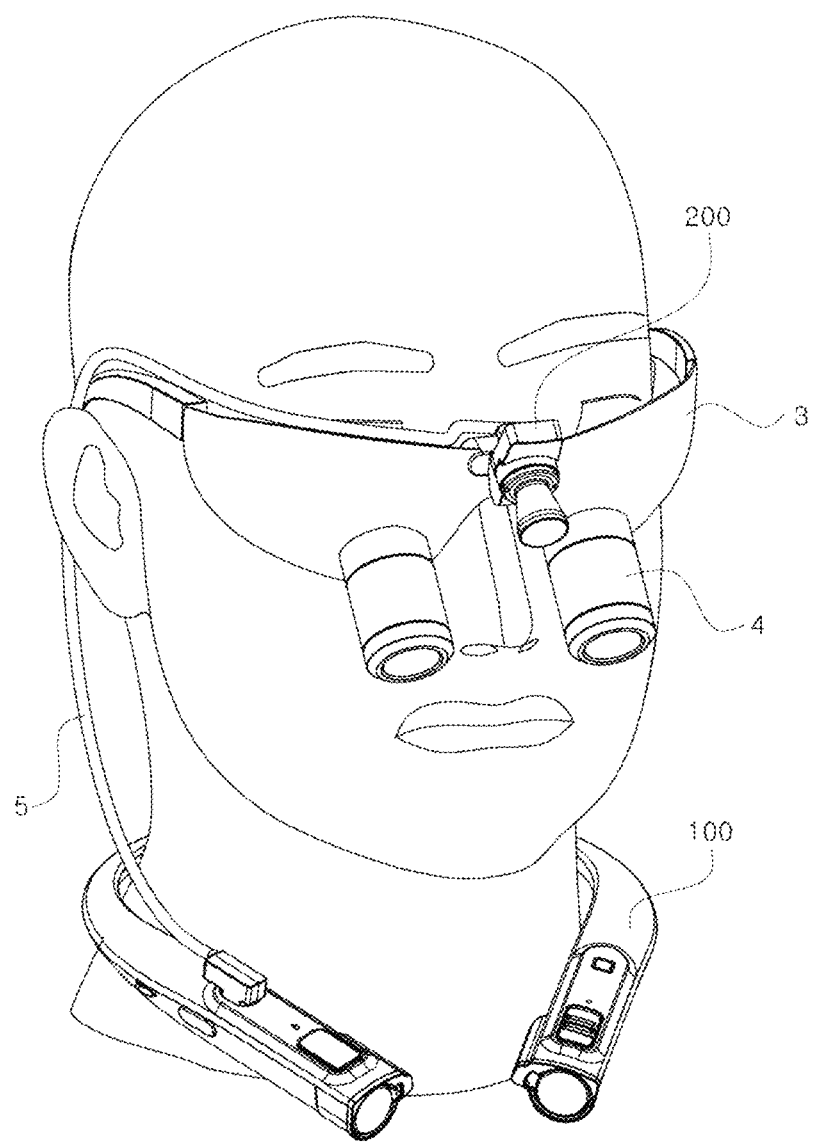

[FIG. 8]
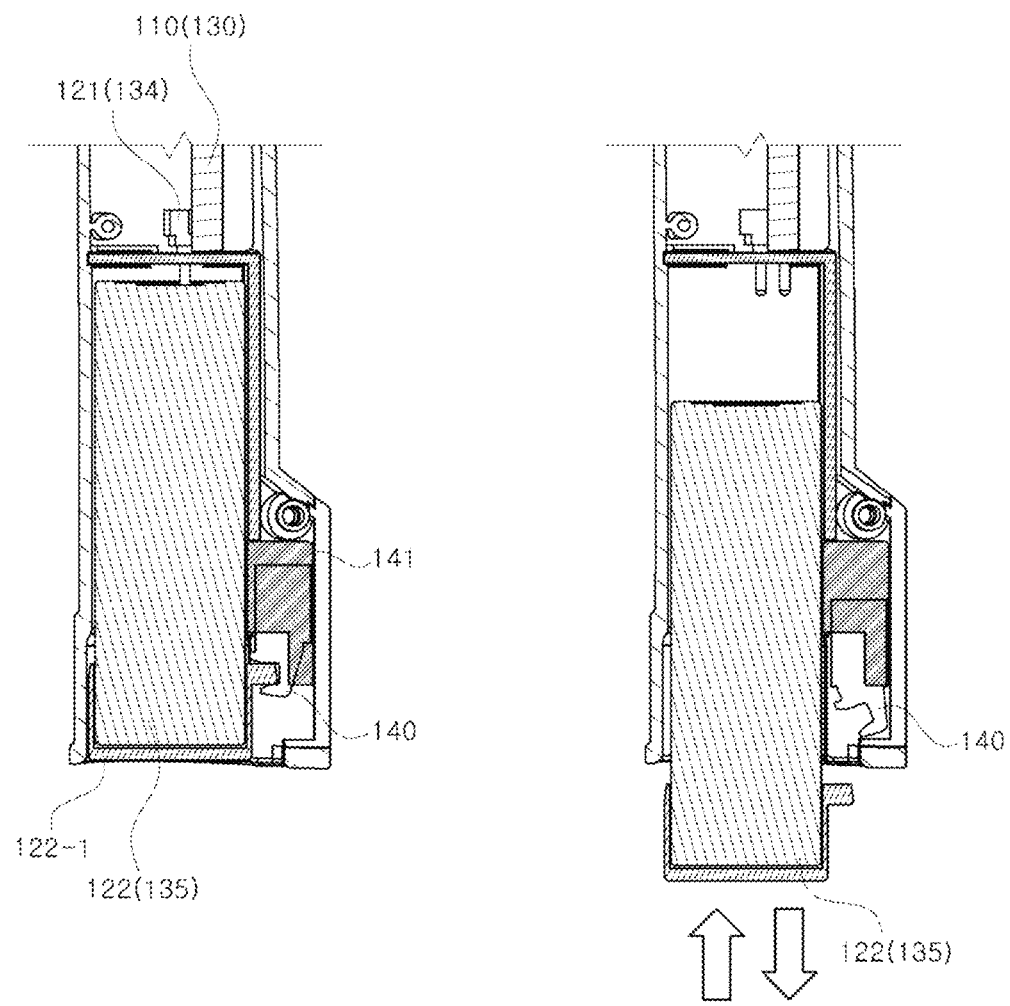
[FIG. 9]
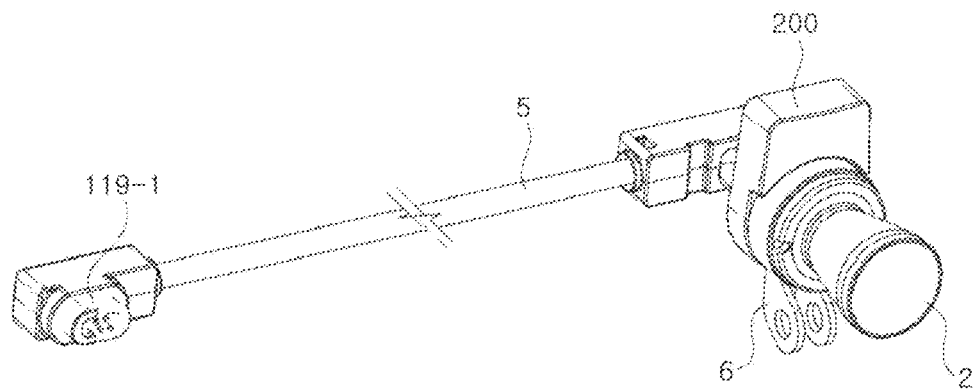

[FIG. 10]
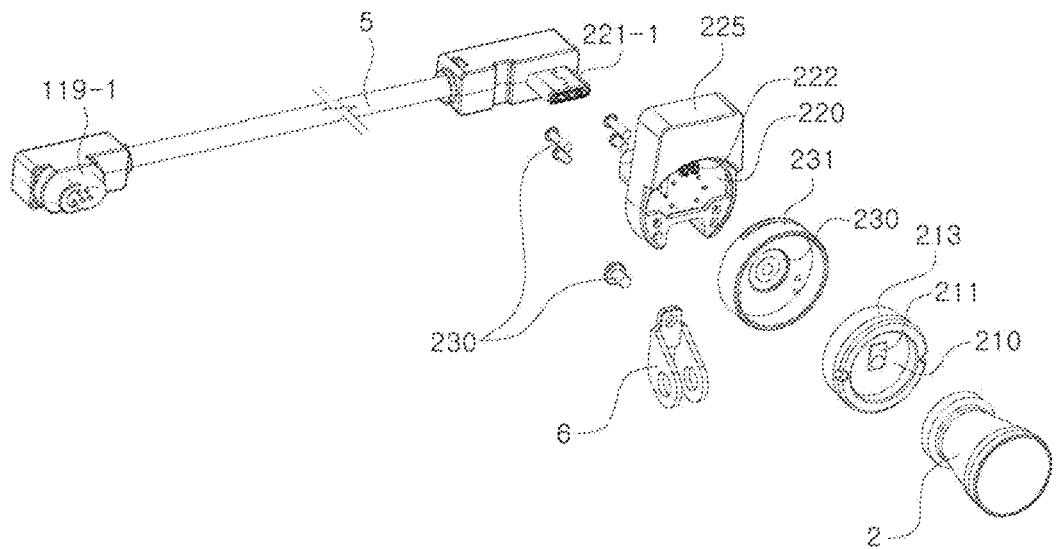
[FIG. 11]
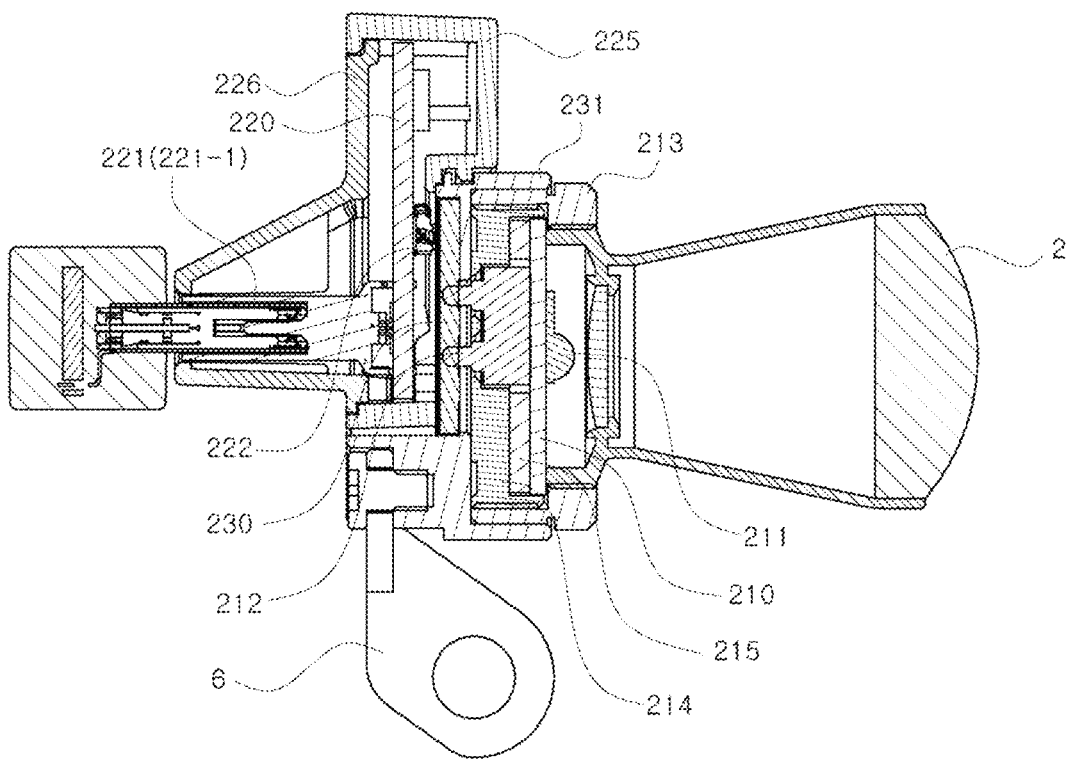

[FIG. 12]
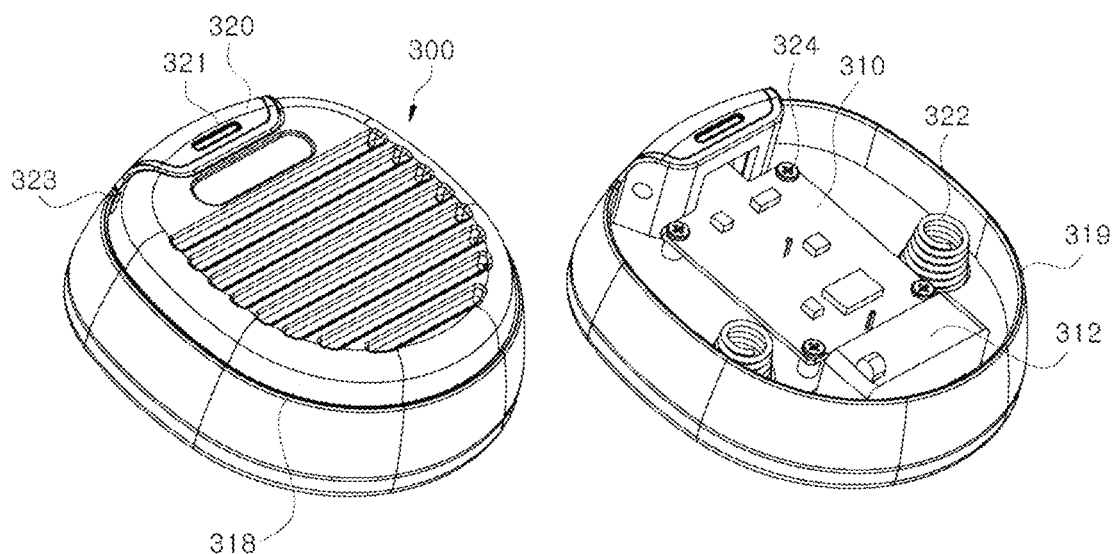
[FIG. 13]
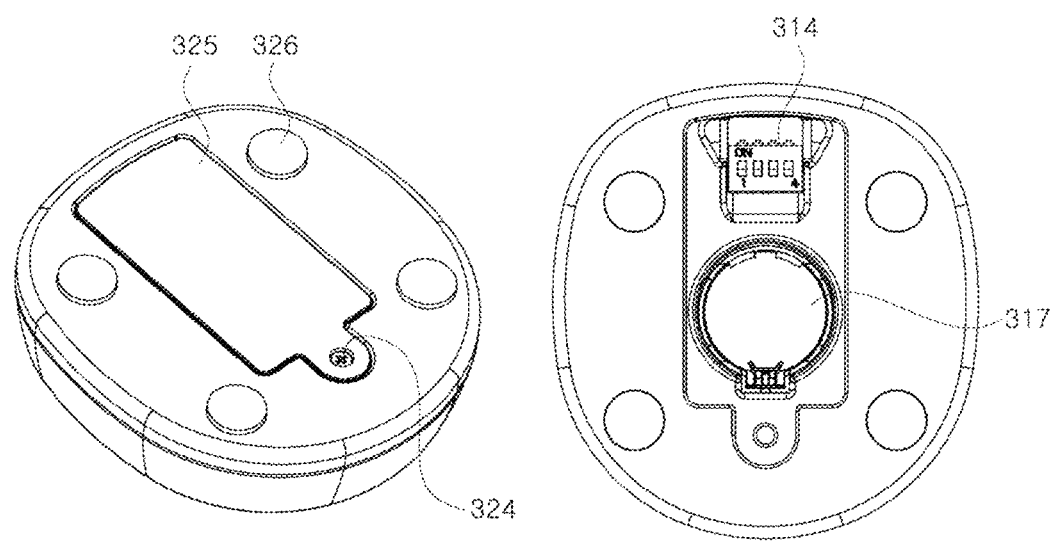

[FIG. 14]
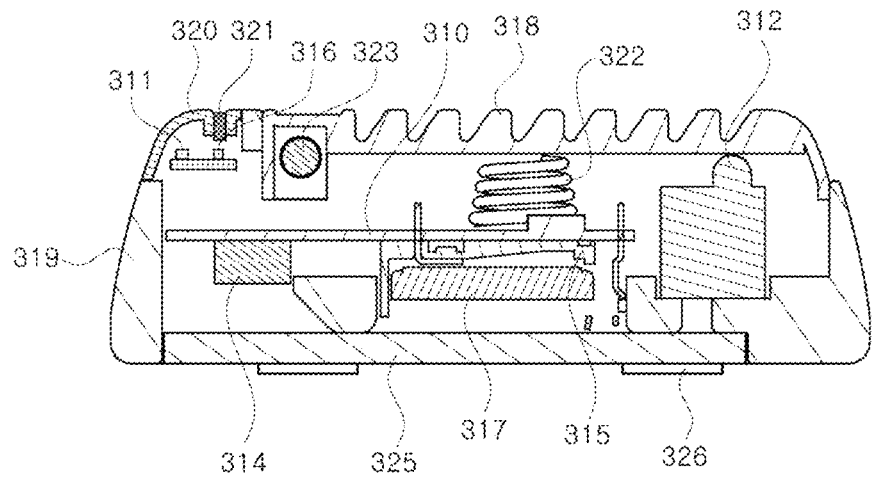
[FIG. 15]
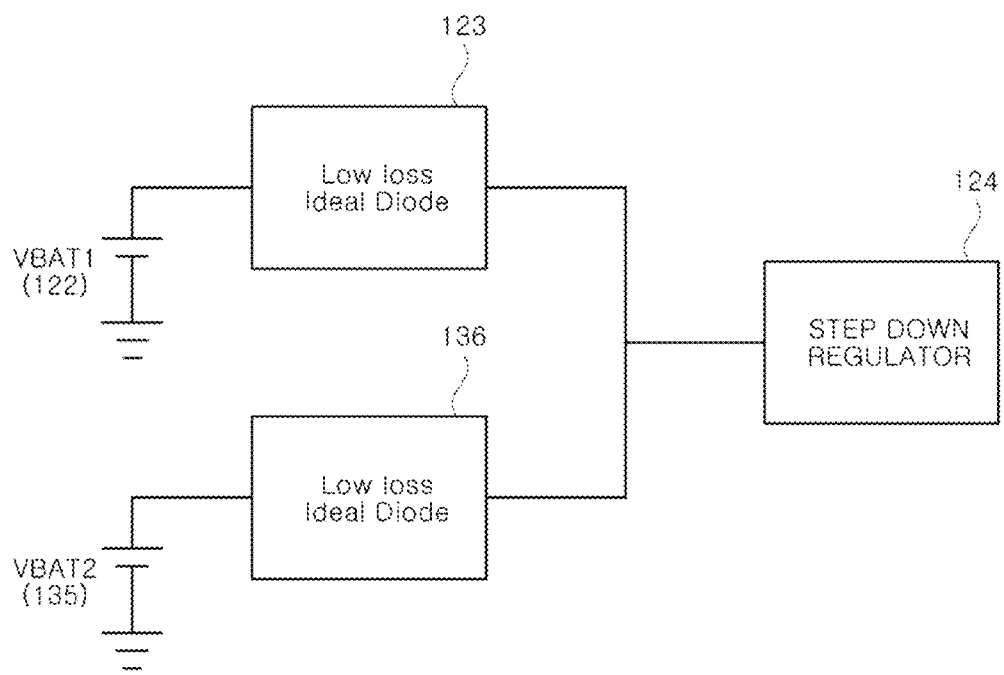

[FIG. 16]
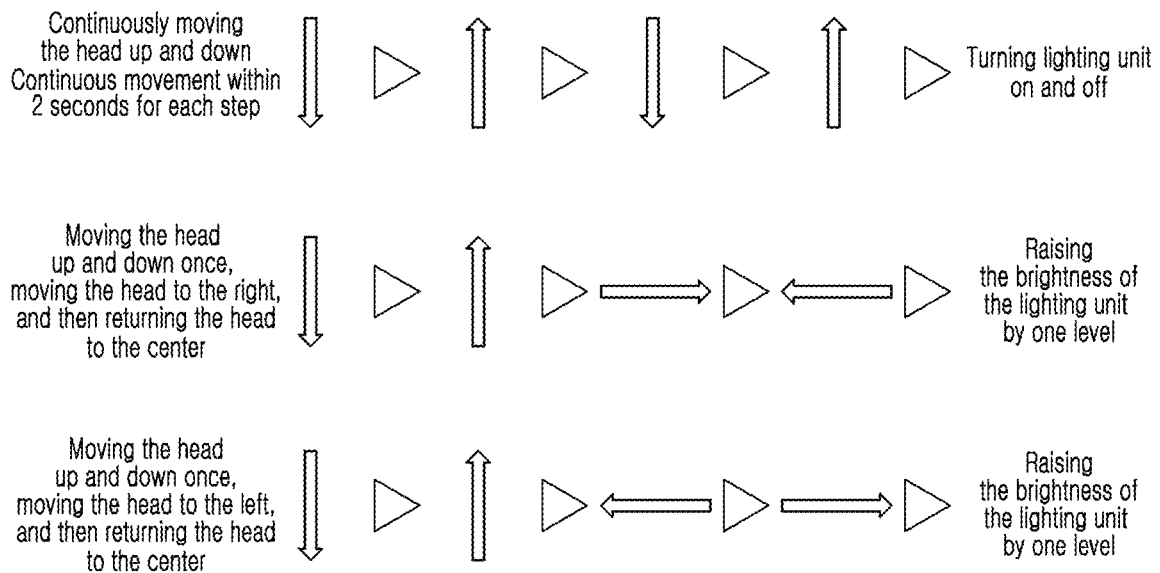
[FIG. 17]
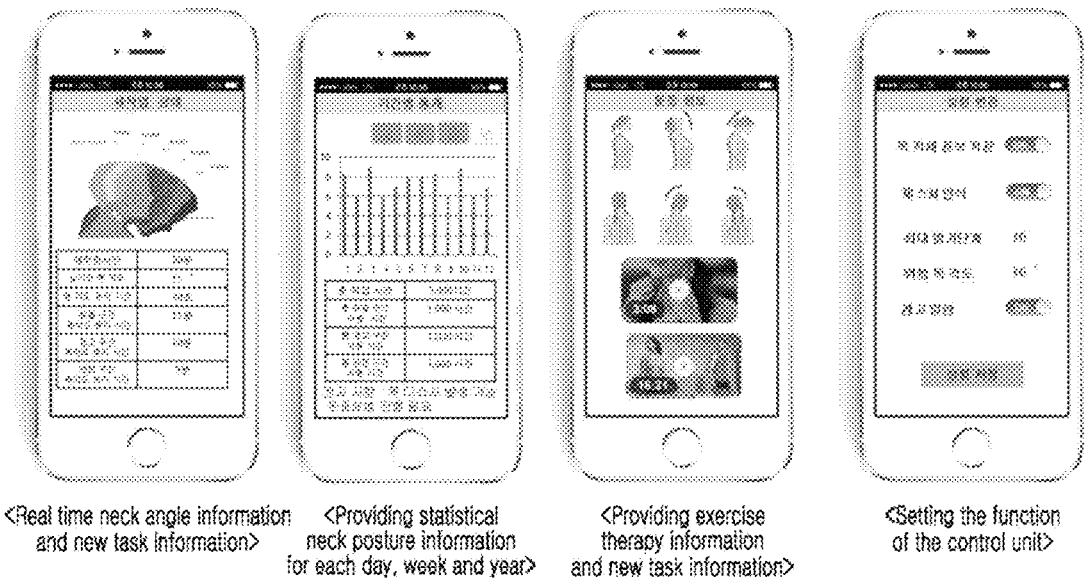

[FIG. 18]
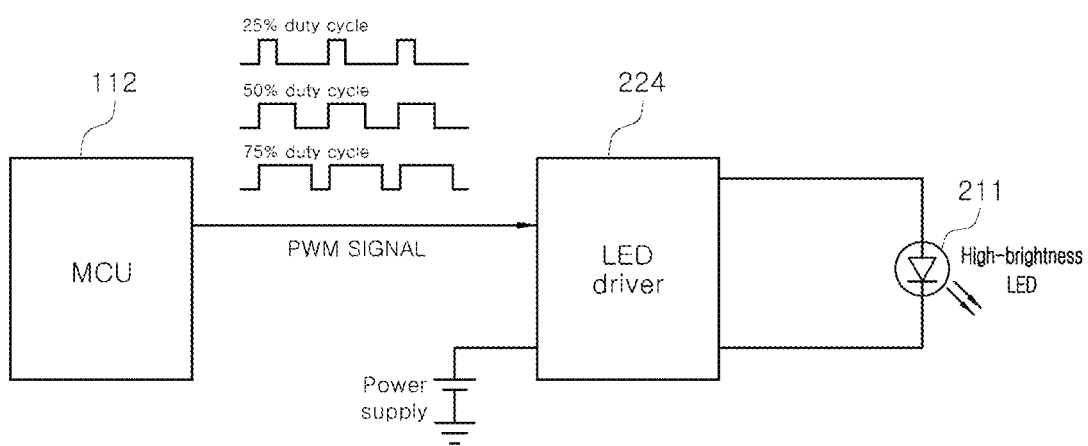

NECKBAND TYPE MEDICAL HEADLIGHT SYSTEM

CROSS-REFERENCE TO RELATED APPLICATION

The present application claims priority under 35 U.S.C. § 119(a) to Korean patent application number 10-2021-0013144 filed on Jan. 29, 2021, which is incorporated herein by reference in its entirety.

TECHNICAL FIELD

The present invention relates to a medical headlight system used when treating or operating a patient in hospital surgery, dentistry, otolaryngology, etc. More specifically, the present invention relates to a neckband-type medical headlight system that can improve the convenience of use and can prevent cross-infection of bacteria or viruses by turning a headlight on and off with the foot instead of the hand and adjusting the brightness of the headlight through the movement of the head without using the hand.

BACKGROUND ART

A medical headlight system for use in patient care and surgery in hospitals usually includes a magnifying glass (also called a 'loupe') attached to glasses or a headset, a headlight configured to emit light, and a controller for controlling the headlight.

The headlight is composed of LEDs having high illuminance, and the controller controls the on/off operation and brightness of the headlight.

Such a medical headlight system may be divided into a wired large-capacity battery headlight system in which a large-capacity battery and a headlight are connected by a cable and the large-capacity battery is worn on the waist, and a wireless small-capacity battery headlight system in which a battery and a controller are miniaturized and integrated into glasses.

FIG. 1 shows an example of a wired large-capacity battery headlight system in which a lighting unit 1 is mounted on glasses 3 equipped with a magnifying glass 4, and an optical unit 2 for collecting the light emitted from the lighting unit 1 in a specific region is provided on the front side of the lighting unit 1.

The lighting unit 1 is mounted on the glasses 3 by a bracket 6. In addition, the lighting unit 1 is connected to a control unit 7 by a power cable 5, and the control unit 7 is provided with an operation switch 71, a large-capacity battery 72 and a control PCB 73.

Accordingly, the medical staff can see a treatment area in a brightly enlarged state through the lighting unit 1 and the magnifying glass 4 while wearing the control unit 7 on the waist.

The above-described wired high-capacity battery headlight system has an advantage that the battery can be used for a long time.

However, in the wired high-capacity battery headlight system, the control unit 7 mounted on the waist and the lighting unit 1 are connected by a power cable 5.

Thus, the wired high-capacity battery headlight system has a drawback that a separate clip (not shown) for fixing the power cable 5 to an operating gown and a band for fixing the power cable 5 to the leg of the glasses 3 are required, and it takes a considerable amount of time to wear and remove the headlight system.

In addition, since the operation button of the lighting unit is frequently touched in the process of using the headlight system, there is a risk of infection by bacteria or viruses in the operating room and treatment room. This may lead to a problem that there may occur cross-contamination in which bacteria or viruses are transferred to third patients and places.

On the other hand, in the wireless small-capacity battery headlight system, as shown in FIG. 2, a small-capacity battery 8, a control PCB and the lighting unit 1 are integrally formed with glasses 3.

The wireless small-capacity battery headlight system has an advantage in that it is easy to mount the headlight because a separate power cable is not required.

However, since the battery is mounted on the glasses, the user's fatigue is increased due to the weight of the battery, and the battery can be used only for 2 to 3 hours due to the limitation in the capacity of the battery.

In addition, since the operation button is frequently touched for the on/off operation of the lighting unit, there is a problem in that contamination and cross-contamination by bacteria in the operating room and treatment room are highly likely to occur.

SUMMARY

In view of the problems inherent in the related art, it is an object of the present invention to allow a user to wear and use a headlight system quickly and easily and to use the headlight system for a long time.

Another object of the present invention is to eliminate the risk of contamination and cross-contamination by various bacteria by eliminating the need for a user to touch and operate a lighting unit with the hand.

A further object of the present invention is to allow a user to easily adjust the brightness of a headlight without touching a control unit with the hand.

A still further object of the present invention is to provide a user with various kinds of information on neck fatigue.

In order to achieve these objects, there is provided a neckband-type medical headlight system, including: a lighting unit and a magnifying glass provided in glasses or a headset; a control unit configured to control the lighting unit; and a battery and a power cable configured to supply electric power to the lighting unit, wherein the control unit for controlling the lighting unit is composed of a neckband type to be seated around a user's neck, and a pedal-type wireless control unit is further provided to enable a user to turn on and off the lighting unit using a foot.

In the system according to the present invention, the neckband-type control unit may include a main PCB provided on one side thereof and an auxiliary PCB provided on the other side thereof.

In the system according to the present invention, the main PCB of the control unit may include an RF antenna for wireless communication with the pedal-type wireless control unit and a smartphone, and a buzzer configured to generate a warning sound for a user's incorrect posture.

In the system according to the present invention, a socket-type magnet connector for allowing one end of the power cable to be coupled with the control unit may be provided on one side of the control unit.

In the system according to the present invention, the battery may include two batteries respectively provided on both ends of the neckband-type control unit and configured to be mounted on and removed from the control unit by a latch-type lock in a push/pull manner.

In the system according to the present invention, a plug-type magnet connector to be coupled with a socket-type magnet connector of the control unit may be provided at one end of the power cable, and a plug-type connector to be coupled with a connector of the lighting unit may be provided at the other end of the power cable.

In the system according to the present invention, the control unit may be provided with two low-loss ideal diodes to preferentially select and use a high-voltage battery among two batteries.

In the system according to the present invention, the lighting unit may be provided with a 9-axis sensor configured to recognize user's movement and control the lighting unit based on the user's movement.

In the system according to the present invention, the 9-axis sensor may include three acceleration sensors and three gyro sensors.

In the system according to the present invention, the lighting unit may be turned on and off when a user moves user's head up and down twice within 2 to 3 seconds.

In the system according to the present invention, the brightness of the lighting unit may be raised by one level when a user moves a user's head up and down once within 2 to 3 seconds, moves the user's head to the right, and then returns the user's head to the center.

In the system according to the present invention, the brightness of the lighting unit may be lowered by one level when a user moves a user's head up and down once within 2 to 3 seconds, moves the user's head to the left, and then returns the user's head to the center.

In the system according to the present invention, the control unit may include a buzzer configured to issue a warning when a user's neck is excessively bent over a certain angle and such a posture is continuously maintained.

In the system according to the present invention, the control unit may be configured to turn the lighting unit on and off or adjust the brightness of the lighting unit through PWM control.

In the system according to the present invention, the system may be linked with a smartphone application to store a user's neck angle and analyze neck fatigue for each date and time.

In the system according to the present invention, the control unit may be configured so that the settings of the control unit can be changed in the smartphone application.

In the system according to the present invention, the pedal-type wireless control unit may include an RF antenna for wireless communication with the control unit, a DIP switch configured to set a unique number to a pedal, a hinge configured to allow an upper cover to rotate at a predetermined angle, a spring configured to support the upper cover, and a battery configured to supply electric power to the pedal-type wireless control unit.

In the system according to the present invention, the malfunction of the headlight system may be prevented by setting a unique value of the DIP switch of the pedal-type wireless control unit and the DIP switch of the control unit.

According to the present invention, the control unit is configured as a neckband type hung around the neck, whereby the user can wear the control unit quickly and conveniently.

In addition, since the length of the power cable for connecting the lighting unit and the control unit is short, there is no need to provide a separate clip or band when wearing the headlight. Therefore, it is possible to shorten the time required for wearing and removing the headlight.

In addition, since the lighting unit is turned on and off by stepping on the pedal with the foot, it is possible to improve the convenience of use.

In addition, since the 9-axis sensor is applied to the lighting unit to adjust the brightness of the headlight by the movement of the head during use, it is not necessary to operate the button by the hand.

In addition, since the control unit can be operated without the use of the hand, it is possible to prevent contamination and cross-contamination by bacteria in the operating room or treatment room.

In addition, since the battery is provided on both sides of the control unit, it is possible to reduce the fatigue of the user due to the weight of the battery and to increase the use time of the headlight.

In addition, since a low-loss ideal diode is provided at the input terminal of the battery power, a reverse current flow due to the use of two batteries can be prevented, and a battery with a high power can be preferentially used.

In addition, even if one of the two batteries is removed, the headlight can be used continuously.

In addition, since each component is modularized, only the corresponding component can be replaced, which makes it possible to simplify the maintenance.

In addition, the heat buffer PCB can prevent the high-temperature heat generated from the LED PCB from being directly transferred to the lighting unit PCB.

In addition, since a point-to-point contact type connector is used when transmitting electrical signals of the respective PCBs, it is possible to minimize heat conduction in the lighting unit using high power.

In addition, since the brightness of the lighting unit is adjusted through the PWM control of the control unit, it is possible to realize the intensity of brightness in various ways without having to use a separate rotary variable resistor.

In addition, the user is warned when the angle of the neck is excessive, it is possible to allow the user to perform treatment in a stable posture.

In addition, the headlight is used in conjunction with the smartphone, it is possible to provide various kinds of information about the user's neck fatigue.

BRIEF DESCRIPTION OF THE DRAWINGS

FIG. 1 is a view showing a wired large-capacity battery type headlight system according to the prior art.

FIG. 2 is a view showing a wireless small-capacity battery type headlight system according to the prior art.

FIG. 3 is a block diagram of a headlight system according to the present invention.

FIG. 4 is a perspective view of a control unit according to the present invention.

FIG. 5 is an internal perspective view of the control unit according to the present invention.

FIG. 6 is a rear perspective view of the control unit according to the present invention.

FIG. 7 is a view showing a wearing state of the headlight according to the present invention.

FIG. 8 is a view showing a battery attachment/detachment structure of the control unit according to the present invention.

FIG. 9 is a perspective view of a lighting unit according to the present invention.

FIG. 10 is an exploded perspective view of the lighting unit according to the present invention.

FIG. 11 is a cross-sectional view of the lighting unit according to the present invention.

FIG. 12 is a perspective view of a pedal-type wireless control unit according to the present invention.

FIG. 13 is a rear view of the pedal-type wireless control unit according to the present invention.

FIG. 14 is a cross-sectional view of the pedal-type wireless control unit according to the present invention.

FIG. 15 is a battery control circuit diagram of the control unit according to the present invention.

FIG. 16 is a view for explaining a method of controlling the lighting unit according to a user's movement in the headlight system according to the present invention.

FIG. 17 is a view showing an application of a smartphone in the headlight system according to the present invention.

FIG. 18 is a view for explaining a PWM control method of the control unit for the lighting unit according to the present invention.

DETAILED DESCRIPTION

A preferred embodiments of the present invention will now be described in detail with reference to FIGS. 3 to 17.

As shown in FIG. 3, the medical headlight system according to the present invention includes a neckband-type headlight control unit 100, a lighting unit 200, and a pedal-type wireless control unit 300.

First, the headlight control unit 100 of the present invention will be described.

As shown in FIGS. 4 to 7, the neckband-type headlight control unit 100 (hereinafter simply referred to as a 'control unit') according to the present invention includes a main PCB (Printed Circuit Board) unit 110 provided on one side, an auxiliary PCB unit 130 provided on the other side, a cable wire 140 configured to electrically and signally connect the main PCB unit 110 and the auxiliary PCB unit 130, a top cover 151 configured to structurally fix these components, a bottom cover 150, an elastic connector 152, and a fastening screw 153.

In the present invention, the control unit 100 is configured in the form of a neckband. Accordingly, the control unit 100 only needs to be hung around the neck, which makes it very easy to wear the headlight.

The main PCB unit 110 includes an MCU (Main Control Unit) 112 configured to control the overall operation of the system, an LED (Light Emitting Diode) 111 configured to indicate the remaining power amount of batteries 122 and 135 and the state of the system, a lock switch 113 configured to prevent a button from being unnecessarily pushed during use, an up/down switch 114 configured to control the brightness of a high-brightness LED 211 of the lighting unit 200, a DIP (Dual Inline Package) switch 115 capable of setting the unique number of a pedal having a signal to be received among signals transmitted from a plurality of pedals, a power button 116 configured to turn on and off the entire power of the control unit 100, a buzzer 117 indicating the operation status of the system, a flash memory 118 configured to record the values of the 9-axis sensor 223 of the lighting unit 200 for each date and time, a connector 119 configured to connect a signal to the lighting unit 200, an RF (Radio Frequency) antenna 120 configured to receives a radio signal transmitted from the pedal-type wireless control unit 300 and perform wireless communication with a smartphone, a contact-type connector 121 configured to receive battery power, and batteries 122 and 135 configured to supply power.

As shown in FIG. 8, two batteries 122 and 135 are mounted on both ends of the control unit 100 and are attached and detached by a latch-type lock 140.

The lower ends of the batteries 122 and 135 are seated in a battery holder 122-1 so that they can be fixed by the latch-type lock 140.

In addition, a protrusion 122-1 is provided on one side of the battery holder 122-1 so that it can be firmly fixed to the latch-type lock 140.

The latch-type lock 140 is configured to be operated in a push-lock/push-release manner. To this end, a compression spring 141 is provided inside the latch-type lock 140, and a free space for lock release is provided at the upper end of the battery.

It is preferable that the LED 111 provided on the main PCB 110 indicates the remaining power amount of the battery through colors. For example, the remaining power amount of the battery may be indicated in three stages, i.e., blue, purple and red.

The buzzer 117 notifies the user of the setting completion state realized by pressing a switch or a button through various sound sources.

The auxiliary PCB 130 is provided on the opposite side of the main PCB 110. The auxiliary PCB 130 includes an LED 131 configured to indicate a connection state with a smartphone, a correction button 132 configured to set an origin reference of the 9-axis sensor, a setting switch 133 configured to set an on/off state of a specific function, a contact-type connector 134 configured to receive battery power, and a battery 135 configured to supply power.

On the rear surface of the control unit 100, as shown in FIG. 6, a DIP switch 115 capable of setting a unique number of a desired pedal among a plurality of pedals is provided.

The DIP switch is configured to prevent malfunction when a plurality of pedal-type wireless control units 300 is applied.

For example, if the numbers of the DIP switches 314 of the plurality of pedal units 300 are set to 0001, 0011, 0111, 1111, etc. and if the number of the DIP switch 115 of the control unit 100 is set to 0001, the control unit 100 responds only to the pedal unit 300 set to 0001 and ignores signals from other pedal switches.

Through the number setting as described above, one control unit 100 and a plurality of pedal units 300 can be dispersed in various places.

In addition, when two or more control units 100 and the pedal-type wireless control units 300 are used in the same space, it is possible to prevent malfunction.

Next, the lighting unit 200 of the present invention will be described with reference to FIGS. 7 and 9 to 11.

The lighting unit 200 according to the present invention is provided in the glasses 3 and is connected to the control unit 100 by the power cable 5. The lighting unit 200 has a function of emitting high-brightness light and recognizing the user's gesture.

The lighting unit 200 includes a lighting unit PCB 220 configured to control the optical unit 2 and the high-brightness LED 211 and recognize the user's gesture using a 9-axis sensor, an LED PCB 210 including an LED 211 configured to emit high-brightness light, a heat buffer PCB 230 configured to allow only electrical signals to be transmitted to the lighting unit PCB 220 while preventing the high-temperature heat generated on the rear surface of the PCB from being directly transferred to the lighting unit PCB 220, and component cover modules 213, 214, 231, 225 and 226.

In addition, the lighting unit 200 includes a socket-type connector 221 configured to receive a control signal from the control unit 100 and receive electric power, an LED driver 224 configured to configured to adjust and maintain the brightness of the high-brightness LED 211 constant, a 9-axis sensor 223 configured to perform a function of recognizing a user's gesture by measuring the angle and rotation degree of the user's neck, the instantaneous amount of movement of the user's neck, etc., and a contact-type connector 222 configured to transmit an electrical signal to the heat buffer PCB 230.

In this regard, the 9-axis sensor 223 preferably includes three acceleration sensors and three gyro sensors.

The heat buffer PCB 230 is located in the middle between the LED PCB 210 and the lighting unit PCB 220 and is configured to allow only electrical signals to be transmitted to the lighting unit PCB 220 while preventing the high-temperature heat generated in the LED PCB 210 from being directly transferred to the lighting unit PCB 220.

A high-power high-brightness LED of more than 1W power consumption is used as the LED 211, and a contact-type connector 212 for connection with the heat buffer PCB 230 is provided on the rear surface of the LED 211.

In addition, as shown in FIG. 9, the lighting unit 200 is connected to the control unit 100 by the power cable 5.

As shown in FIG. 10, the power cable 5 includes a plug-type connector 119-1 fastened to the connector 119 of the main PCB, and a plug-type connector 221-1 fastened to the connector 221 of the lighting unit PCB.

The power cable 5 may have problems such as disconnection and the like during use. Only the damaged cable can be easily replaced by using the connectors.

Furthermore, it is preferable that the connectors are of a magnet type so that the connectors can be attached and detached with ease.

In addition, each component is modularized in the present invention. Therefore, when a defect occurs in each module, only the corresponding component can be replaced and used.

Moreover, since the transmission of an electric current and a signal to each PCB is performed by the point-to-point contact type connectors 212 and 222, it is possible to minimize heat conduction.

Next, the pedal-type wireless control unit 300 of the present invention will be described.

As shown in FIGS. 3 and 12 to 14, the pedal-type wireless control unit 300 according to the present invention includes an RF antenna 311 configured to wirelessly transmits the user's press information to the control unit 100, a switch 312 configured to recognize the press information of the upper cover 318 of the pedal, an MCU 313 configured to control the pedal PCB 310 by grasping the press information of the upper cover 318 and recognizing the unique information of the pedal, a DIP switch 314 configured to set unique values to distinguish a plurality of pedal-type wireless control units from each other, an LED 316 configured to notify a user of a state that the upper cover is pressed and the RF signal is transmitted, a battery 317 configured to supply electric power to the pedal PCB 310, and a connector 315 configured to connect the power supply of the battery 317 to the pedal PCB 310.

The pedal-type wireless control unit 300 is placed on the floor during use. When the user presses the upper cover 318 with the foot, the switch 312 is energized. The MCU 313 transmits the pressed state to the control unit 100 through the RF antenna 311.

At this time, the MCU 313 transmits the set value of the DIP switch 314 together with the press information of the switch. Accordingly, the control unit 100 is operated only when it has the same set value as the pedal-type wireless control unit 300.

Since the upper cover 318 in contact with the user's foot and the lower cover 319 for fixing the pedal PCB are made of a metallic material such as aluminum or the like, the radio wave of the RF antenna 311 may be disturbed.

Accordingly, it is preferable that the RF antenna 311 is configured as a separate PCB and placed on the upper end of the pedal-type wireless control unit 300, and the plastic cover 320 having no problem in radio wave communication is applied.

In addition, in the present invention, the LED 316 for notifying the user of the pressed state of the pedal and the RF antenna 311 are configured as separate PCBs and are mounted on the upper corner of the pedal having no metal.

In order to quickly restore the pressed state of the upper cover of the pedal unit, a compression spring 322 is provided inside the pedal unit, and a hinge member 323 is provided on one side of the pedal unit to allow rotation of the upper cover. In addition, an anti-slip pad 326 is provided at the bottom of the pedal unit.

As shown in FIG. 13, a DIP switch 314 for setting a unique set value is provided on the rear surface of the pedal. By using the DIP switch 314, the user may give various setting values.

In the present invention, as shown in FIG. 15, low-loss ideal diodes 123 and 136 are provided at the battery power input portion of the main PCB 110 of the control unit 100 in order to prevent a reverse current flow which may otherwise be caused by the use of two batteries.

The low-loss ideal diodes are electrical devices that allows a current to flow only in a specific direction. The low-loss ideal diodes may make it possible to preferentially use the electric power of the battery having a high voltage.

In addition, even if one battery is removed, the electric power can be supplied continuously through the other battery.

In the present invention, as shown in FIG. 18, the MCU 112 of the control unit and the LED driver 224 of the lighting unit are signally connected through the power cable 5, and the MCU 112 may control the LED driver 224 through signal modulation using a pulse width modulation (PWM) method.

That is, the LED driver 224 may adjust the amount of current applied to the LED 211 according to the duty cycle of PWM, thereby adjusting the brightness.

Through the above-described control method, it is possible to variously realize the brightness intensity of the high-brightness LED 211 without having to use a separate rotary variable resistor.

Hereinafter, a process of using the headlight system according to the present invention will be described.

As shown in FIG. 7, the headlight user wears glasses equipped with the lighting unit 200 and the magnifying glass 4 on the eyes and wears the control unit 100 on the neck.

At this time, the control unit 100 and the lighting unit 200 are connected to each other by the power cable 5. The pedal type wireless control unit 300 is placed on the floor.

When the user presses the power button 116 for a certain period of time, electric power is applied to the entire system, and the MCU 112 of the control unit 100 controls the LED driver 224 of the lighting unit 200, whereby the high-brightness LED 211 is supplied with electric power to emit light.

Then, when the up-down switch is moved up and down, the MCU modulates a signal through PWM and sends the signal to the LED driver 224 so that the LED driver recognizes the signal and adjusts the brightness of the LED.

At this time, it is preferable to set the lock settings for various switches or buttons using the lock switch 113 so that the light is not turned off unintentionally during surgery or medical treatment.

The mounting position and direction of the lighting unit may be different for each user. Thus, the origin of the 9-axis sensor of the lighting unit PCB is also changed.

Therefore, the user needs to reset the origin of the 9-axis sensor based on the mounting state after mounting the lighting unit on the glasses.

To this end, the user presses the correction button 132 for a predetermined time so that the MCU 112 performs a series of tasks.

In addition, the user may activate or deactivate the setting switch 133 to perform tasks such as gesture recognition in the 9-axis sensor, neck angle storage, and paring connection of smartphone.

When the setting switch 133 is activated, the gesture function of the 9-axis sensor 223 is started. The 9-axis sensor 223 measures the user's neck angle, neck rotation, instantaneous movement speed, and the like, and transmits the measurement result to the MCU 112.

Then, the MCU 112 adjusts the brightness of the lighting unit or turns on and off the lighting unit based on the measurement result.

Hereinafter, a process of turning on and off the lighting unit or adjusting the brightness of the lighting unit according to the user's gesture will be described with reference to FIG. 16.

First, when the user moves user's head up and down twice within 2 to 3 seconds while wearing the headlight, the lighting unit is turned on and off alternately.

At this time, if the time of moving the user's head exceeds a predetermined time or is not an accurate vertical movement, the movement is not recognized.

When the user gestures to move user's head up and down once within 2 to 3 seconds, move the head to the right, and then return the head to the center, the lighting unit raises the brightness by one level.

When the user gestures to move user's head up and down once within 2 to 3 seconds, move the head to the left, and then return the head to the center, the lighting unit lowers the brightness by one level.

In addition, the MCU stores the neck angle information of the acceleration sensor in the flash memory 118 for each date and time and transmits the information by calling the smart phone APP (Application) 1001 when necessary.

Based on the user's neck angle information, the smartphone APP statistically analyzes the neck fatigue caused by long neck bending and provides the user with various kinds of information such as appropriate exercise therapy and the like.

That is, as shown in FIG. 17, the smartphone APP may inform the user of the user's neck angle and the neck use time in a dangerous neck angle section or a warning neck angle section in real time in a newly started task and may provide the user with the statistical information for days, weeks, months, and years.

Meanwhile, the dangerous neck angle section, the issuance or non-issuance of warning, the brightness level, etc. may be set in the smartphone APP 1001 and may be applied to the control unit 100 through RF antenna.

According to the present invention, since the control unit is configured as a neckband type, it is very easy to wear and use the headlight.

In particular, since the length of the power cable connecting the control unit and the lighting unit is shortened, the inconvenience caused by the power cable can be minimized while adopting the wired battery system.

In addition, the lighting unit can be turned on and off with the foot without having to use the hand, and the brightness of the lighting unit can be adjusted only by the movement of the head detected by the 9-axis sensor.

This eliminates the need for the user to manually operate the headlight during surgery or treatment, thereby eliminating the risk of contamination and cross-contamination by various bacteria.

In addition, the use time of the headlight system can be increased by using two batteries, and the battery with higher voltage power can be preferentially used by providing the low-loss ideal diode.

In addition, by applying the DIP switch, it is possible to prevent malfunction of the control unit and the pedal-type wireless control unit.

In addition, the power cable can be easily assembled to the control unit and the lighting unit by means of the magnet connectors, and the replacement and maintenance of components becomes easy by modularizing each component.

In addition, by linking the headlight with the smartphone, it is possible to provide various kinds of information about the movement of the user's neck.

While the preferred embodiments of the present invention have been described above, the present invention is not limited to the above-described embodiments. Various modifications and changes may be made without departing from the scope and spirit of the present invention defined in the claims.

What is claimed is:

1. A neckband-type medical headlight system, comprising:
    a lighting unit and a magnifying glass provided in glasses or a headset;
    a control unit configured to control the lighting unit; and
    a battery and a power cable configured to supply electric power to the lighting unit,
    wherein the control unit for controlling the lighting unit is composed of a neckband type to be seated around a user's neck, and
    a pedal-type wireless control unit is further provided to enable a user to turn on and off the lighting unit using a foot,
    and wherein the neckband-type headlight control unit includes a main PCB provided on one side, an auxiliary PCB unit provided on the other side, a cable wire configured to electrically and signally connect the main PCB unit and the auxiliary PCB unit, a top cover configured to structurally fix these components, a bottom cover, an elastic connector, and a fastening screw,
    and wherein the main PCB unit includes an MCU configured to control the overall operation of the system, an LED configured to indicate the remaining power amount of batteries and the state of the system, a lock switch configured to prevent a button from being unnecessarily pushed during use, an up/down switch configured to control the brightness of a high-brightness LED of the lighting unit, a DIP switch capable of setting the unique number of a pedal having a signal to be received among signals transmitted from a plurality of pedals, a power button configured to turn on and off the entire power of the control unit, a buzzer indicating the operation status of the system, a flash memory configured to record the values of the 9-axis sensor of the lighting unit for each date and time, a connector configured to connect a signal to the lighting unit, an RF antenna configured to receives a radio signal transmitted from the pedal-type wireless control unit and perform wireless communication with a smartphone, a contact-type connector configured to receive battery power, and batteries configured to supply power, and wherein the auxiliary PCB is provided on the opposite side of the main PCB and the auxiliary PCB includes an LED configured to indicate a connection state with a smartphone, a correction button configured to set an origin reference of the 9-axis sensor, a setting switch configured to set an on/off state of a specific function, a contact-type connector configured to receive battery power, and a battery configured to supply power, and wherein the DIP switch is provided on the rear surface of the control unit and capable of setting a unique number of a desired pedal among a plurality of pedals, and wherein the control unit is provided with two low-loss diodes to preferentially select and use a high-voltage battery among two batteries, and wherein the lighting unit includes a lighting unit PCB configured to control the optical unit and the high-brightness LED and recognize the user's gesture using a 9-axis sensor, an LED PCB including an LED configured to emit high-brightness light, a heat buffer PCB configured to allow only electrical signals to be transmitted to the lighting unit PCB while preventing the high-temperature heat generated on the rear surface of the PCB from being directly transferred to the lighting unit PCB, and component cover modules, and wherein the lighting unit includes a socket-type connector configured to receive a control signal from the control unit and receive electric power, an LED driver configured to configured to adjust and maintain the brightness of the high-brightness LED constant, a 9-axis sensor configured to perform a function of recognizing a user's gesture by measuring the angle and rotation degree of the user's neck, the instantaneous amount of movement of the user's neck, and a contact-type connector configured to transmit an electrical signal to the heat buffer PCB, and wherein the system is linked with a smartphone application to store a user's neck angle and analyze neck fatigue for each date and time, and wherein the pedal-type wireless control unit includes an RF antenna configured to wirelessly transmits the user's press information to the control unit, a switch configured to recognize the press information of the upper cover of the pedal, an MCU configured to control the pedal PCB by grasping the press information of the upper cover and recognizing the unique information of the pedal, a DIP switch configured to set unique values to distinguish a plurality of pedal-type wireless control units from each other, an LED configured to notify a user of a state that the upper cover is pressed and the RF signal is transmitted, a battery configured to supply electric power to the pedal PCB, and a connector configured to connect the power supply of the battery to the pedal PCB, and wherein the lighting unit can be turned on and off with the foot without having to use the hand, and the brightness of the lighting unit can be adjusted only by the movement of the head detected by the 9-axis sensor, and wherein it is possible to prevent malfunction of the control unit and the pedal-type wireless control unit by applying the DIP switch, and wherein the power cable can be easily assembled to the control unit and the lighting unit by means of the magnet connectors.

2. The system of claim 1, wherein the battery includes two batteries respectively provided on both ends of the neckband-type control unit and configured to be mounted on and removed from the control unit by a latch-type lock in a push/pull manner, and wherein the two batteries are mounted on both ends of the control unit and are attached and detached by a latch-type lock, and a protrusion is provided on one side of the battery holder so that it can be firmly fixed to the latch-type lock, and the latch-type lock is configured to be operated in a push-lock/push-release manner.

3. The system of claim 1, wherein a plug-type magnet connector to be coupled with a socket-type magnet connector of the control unit is provided at one end of the power cable, and a plug-type connector to be coupled with a connector of the lighting unit is provided at the other end of the power cable, and wherein the power cable includes a plug-type connector fastened to the connector of the main PCB, and a plug-type connector fastened to the connector of the lighting unit PCB, and wherein the connectors are of a magnet type so that the connectors can be attached and detached with ease.

4. The system of claim 1, wherein the 9-axis sensor includes three acceleration sensors and three gyro sensors.

5. The system of claim 4, wherein the control unit includes a buzzer configured to issue a warning when a user's neck is excessively bent over a certain angle and such a posture is continuously maintained.

6. The system of claim 1, wherein the control unit is configured to turn the lighting unit on and off or adjust the brightness of the lighting unit through PWM control.

* * * * *